(12) United States Patent
Ferguson et al.

(10) Patent No.: US 7,700,562 B2
(45) Date of Patent: Apr. 20, 2010

(54) USE OF —FURIN—"CONVERTASE" INHIBITORS IN THE TREATMENT OF FIBROSIS AND SCARRING

(75) Inventors: Mark William James Ferguson, Derbyshire (GB); Georg Brunner, Muenster (DE)

(73) Assignee: Renovo Limited, Manchester (GB)

( * ) Notice: Subject to any disclaimer, the term of this patent is extended or adjusted under 35 U.S.C. 154(b) by 242 days.

(21) Appl. No.: 10/522,222

(22) PCT Filed: Jul. 23, 2003

(86) PCT No.: PCT/GB03/03159

§ 371 (c)(1), (2), (4) Date: Jan. 24, 2005

(87) PCT Pub. No.: WO2004/009113

PCT Pub. Date: Jan. 29, 2004

(65) Prior Publication Data

US 2006/0052309 A1     Mar. 9, 2006

(30) Foreign Application Priority Data

Jul. 24, 2002  (GB) ............................ 0217136.1

(51) Int. Cl.
*A61K 38/06* (2006.01)
*A61F 13/00* (2006.01)
*A61D 9/00* (2006.01)

(52) U.S. Cl. .................... 514/18; 530/330; 930/250; 602/42; 604/46; 606/214

(58) Field of Classification Search ............ None
See application file for complete search history.

(56) References Cited

U.S. PATENT DOCUMENTS

| | | | |
|---|---|---|---|
| 5,439,824 A | | 8/1995 | Brantly |
| 5,874,479 A | * | 2/1999 | Martin ................. 514/724 |
| 6,262,020 B1 | | 7/2001 | Lezdey |
| 2003/0087827 A1 | * | 5/2003 | Lindberg et al. ......... 514/14 |

FOREIGN PATENT DOCUMENTS

| | | | |
|---|---|---|---|
| CA | 2312109 | * | 12/2001 |
| CA | 2312109 A1 | * | 12/2001 |
| EP | 0 356 595 | | 3/1990 |
| EP | 0 363 284 | | 4/1990 |
| EP | 0 968 723 | | 1/2000 |
| GB | 2 265 310 | | 9/1993 |
| GB | 2 324 960 | | 11/1998 |
| WO | WO-92/17206 | | 10/1992 |
| WO | WO-9217206 | * | 10/1992 |
| WO | WO-95/02579 | | 1/1995 |
| WO | WO-00/40227 | * | 7/2000 |

OTHER PUBLICATIONS

[Retrived from] 'http://www.nlm.nih.gov/medlineplus/ency/article/000484.htm' 2007, 4 pages [retrieved on May 30, 2007].*
[Retrived from] 'http://www.pulmonaryfibrosis.org/ipf.htm'2007, 2 pages[retrieved on May 24, 2007].*
[Retrived from]'http://en.wikipedia.org/wiki/Cirrhosis'2007, 8 pages [Retrieved on May 30, 2007].*
Pearton, et al., 2001, Exp Dermatology, 10, 193-203.*
[Retrieved from] http://encarta.msn.com/encnet/features/dictionary/DictionaryResults.aspx?refid=1861720920, 2008, 2 pages [Retrieved on Nov. 16, 2008].*
UK Patent Office Search Report for GB 0217136.1, mailed on Dec. 19, 2002, 1 page.
Cameron et al., J. of Biological Chemistry (2000) 275:36741-36749.
Chan et al., PNAS USA (1992) 89:6678-6682.
Dubois et al., J. of Biological Chemistry (1995) 270:10618-10624.
International Search Report for PCT/GB03/03159, mailed on Nov. 20, 2003, 6 pages.
O'Kane et al., Int. J. Biochem. & Cell Biology (1997) 29:63-78.
Pearton et al., Experimental Dermatology (2001) 10:193-203.
Sha et al., Mol. Endocrinology (1989) 3:1090-1098.
Shah et al., Journal of Cell Science (1995) 108:985-1002.
Shapiro et al., J. Histochem. Cytochem. (1997) 45:3-12.
Tomlinson et al., Methods in Molecular Biology (2003) 225:249-260.

* cited by examiner

*Primary Examiner*—Andrew D Kosar
*Assistant Examiner*—Satyanarayana R Gudibande
(74) *Attorney, Agent, or Firm*—Foley & Lardner LLP (57) ABSTRACT

The present invention relates to use of convertase inhibitors for the reduction of scarring during the healing of wounds and also for reducing fibrosis in the treatment of fibrotic conditions.

5 Claims, 4 Drawing Sheets

USE OF —FURIN—"CONVERTASE" INHIBITORS IN THE TREATMENT OF FIBROSIS AND SCARRING

This application claims priority under 35 U.S.C. § 119 to PCT/GB2003/003159, filed 23 Jul. 2003, which designates the U.S. and which claims priority to Great Britain Application 0217136.1, filed 24 Jul. 2002, which are incorporated herein by reference.

The present invention relates to wound healing and also to regulating fibrosis in the treatment of conditions in which fibrosis is a major mechanism of tissue repair or where excessive fibrosis leads to pathological derangement and malfunctioning of tissue.

Wound healing in adults is a complicated reparative process. The term "wound" as used herein is exemplified by, but not limited to, injuries to the skin. Other types of wound can involve damage, injury or trauma to an internal tissue or organ such as the lung, kidney, heart, gut, tendons or liver.

The healing process in skin wounds typically begins with a haemostatic response initiated by damage to blood vessels in the skin. During this process platelets and a number of factors present in the blood contribute to the formation of a clot that prevents further blood loss. Factors released during this process, particularly by the degranulation of platelets, then cause recruitment of a variety of specialised cells to the site of the wound that are in turn involved in extracellular matrix and basement membrane deposition, angiogenesis, selective protease activity and re-epithelialisation. An important component of the healing process in adult mammals is the stimulation of fibroblasts to generate the extracellular matrix. This extracellular matrix constitutes a major component of the connective tissue that develops to repair the wound area.

The connective tissue that forms during the healing process is often fibrous in nature and commonly forms into a connective tissue scar (a process known as fibrosis).

A scar is an abnormal morphological structure resulting from a previous injury or wound (e.g. an incision, excision or trauma). Scars are composed of a connective tissue which is predominately a matrix of collagen types 1 and 3 and fibronectin. The scar may consist of collagen fibres with an abnormal organisation (as seen in scars of the skin) or it may be an abnormal accumulation of connective tissue (as seen in scars of the central nervous system). Most scars consist of abnormally organised collagen and also excess collagen. In man, in the skin, scars may be depressed below the surface or elevated above the surface of the skin. Hypertrophic scars represent a severe form of normal scarring. They are elevated above the normal surface of the skin and contain excessive collagen arranged in an abnormal pattern. Keloids are another form of pathological scarring in which the scar is not only elevated above the surface of the skin but also extends beyond the boundaries of the original injury. In a keloid there is excessive connective tissue that is organised in an abnormal fashion predominately in whirls of collagenous tissue. There are genetic predispositions to the formation of both hypertrophic scars and keloids. These aberrant forms of scarring are particularly common in Afro-Caribbean and Mongoloid races.

There are many instances where the regulation of scar formation is of primary importance when considering the outcome of wound healing. Examples of such situations are scars of the skin where excessive scarring may be detrimental to tissue function, particularly in contexts where scar contracture occurs (for instance skin burns and wounds that impair flexibility of a joint). The reduction of scarring to the skin when cosmetic considerations are important is also highly desirable. In the skin hypertrophic or keloid scars can cause functional and cosmetic impairment and there is a need to prevent their occurrence. Scarring resulting from skin grafts in both donor sites and from the application of artificial skin can also be problematic and need to be minimised or prevented.

As well as scars of the skin, internal scarring or fibrosis can be highly detrimental and specific examples include:

(i) Within the central nervous system, glial scarring can prevent neuronal reconnection (e.g. following neurosurgery or penetrating injuries of the brain).

(ii) Scarring in the eye can be detrimental. In the cornea, scarring can result in abnormal opacity and lead to problems with vision or even blindness. In the retina, scarring can cause buckling or retinal detachment and consequently blindness. Scarring following wound healing in operations to relieve pressure in glaucoma (e.g. glaucoma filtration surgery) results in the failure of the surgery whereby the aqueous humour fails to drain and hence the glaucoma returns.

(iii) Scarring in the heart (e.g. following surgery or myocardial infarction) can give rise to abnormal cardiac function.

(iv) Operations involving the abdomen or pelvis often result in adhesion between viscera. For instance, adhesions between elements of the gut and the body wall may form and cause twisting in the bowel loop leading to ischaemia, gangrene and the necessity for emergency treatment (untreated they may even be fatal). Likewise, trauma or incisions to the guts can lead to scarring and scar contracture to strictures which cause occlusion of the lumen of the guts which again can be life threatening.

(v) Scarring in the pelvis in the region of the fallopian tubes can lead to infertility.

(vi) Scarring following injury to muscles can result in abnormal contraction and hence poor muscular function.

(vii) Scarring or fibrosis following injury to tendons and ligaments can result in serious loss of function.

Related to the above is the fact that there are a number of medical conditions known as fibrotic disorders in which excessive fibrosis leads to pathological derangement and malfunctioning of tissue. Fibrotic disorders are characterised by the accumulation of fibrous tissue (predominately collagens) in an abnormal fashion within the tissue. Accumulation of such fibrous tissues may result from a variety of disease processes. These diseases do not necessarily have to be caused by surgery, traumatic injury or wounding. Fibrotic disorders are usually chronic. Examples of fibrotic disorders include cirrhosis of the liver, liver fibrosis, glomerulonephritis, pulmonary fibrosis, scleroderma, myocardial fibrosis, fibrosis following myocardial infarction, central nervous system fibrosis following a stroke or neuro-degenerative disorders (e.g. Alzheimer's Disease), proliferative vitreoretinopathy (PVR), restenosis (for example following angioplasty) and arthritis. There is therefore also a need for medicaments which may be used for the treatment of such conditions by regulating (i.e. preventing, inhibiting or reversing) fibrosis/scarring in these fibrotic disorders.

Whilst the above considerations mainly apply to conditions, disorders or diseases of man it will be appreciated that wound healing, scarring and fibrotic disorders can also be problematic in other animals, particularly veterinary or domestic animals (e.g. horses, cattle, dogs, cats etc). For instance abdominal wounds or adhesions are a major reason for having to put down horses (particularly race horses), as are tendon and ligament damage leading to scarring or fibrosis.

There have been several recent developments in the fields of wound healing, scarring and fibrotic disorders. Some of these developments revolve around the recent understanding that an array of cytokines and growth factors is intimately involved in the repair of wounded tissue. In particular, members of the Transforming Growth Factor β (TGF-β) superfamily have been found to play an important role in wound healing. At least 25 molecules are known to be members of the TGF-β superfamily. These include a number of cytokines such as TGF-βs 1 to 5, the DVR group (e.g. dpp and Vg1), Bone Morphogenetic Proteins, Nodal, Activin and Inhibin.

TGF-βs are often secreted from cells in an inactive form known as latent TGF-β. Latent TGF-β consists of an N terminal Latency Associated Peptide (LAP) and the TGF-β and is also referred to as the Small Latent Complex. Additionally the Small Latent Complex can bind to another peptide (derived from a different gene) of variable size called Latent TGF-β Binding Protein (LTBP) in which case the entire complex is known as the Large Latent TGF-β Complex.

Latent TGF-β is activated when the TGF-β is caused to be dissociated from the LAP. This dissociation may be coordinated at a mannose-6-phosphate/Insulin Like Growth Factor II receptor (M6P-R) and involve proteases such as plasmin, the substrates being associated at the cell surface by tissue transglutaminase. Free radicals and reactive oxygen species can also activate TGF-β by causing dissociation from the LAP.

TGF-β (particularly TGF-$β_1$ and TGF-$β_2$) promotes wound healing but is also associated with increased scar formation and fibrosis. Clinical interest in the modulation of TGF-β has been associated with inhibiting its activity in order to reduce scar formation (although this may compromise the rate of wound healing). For instance, WO 92/17206 discloses neutralising agents that inhibit the activity of TGF-$β_1$ and TGF-$β_2$ and are particularly beneficial for reducing scar formation.

Another development involves the use of mannose-6-phosphate for use in treating fibrotic disorders associated with accumulation of extracellular matrix and with elevated levels of Transforming Growth Factors $β_1$ or $β_2$ (GB-A-2,265,310). Mannose-6-phosphate is believed to interfere with the conversion of latent forms of these Transforming Growth Factors into their active form.

Despite such advances there remains a need to continue to develop medicaments that may be used to modulate the healing of wounds, scarring and fibrosis. In particular there is a need for medicaments which do not compromise the rate of wound healing or quality of scar in favour of one or the other.

As discussed more fully below, the invention relates in its broadest aspect to the use of convertase inhibitors for the treatment of wounds.

According to a first aspect of the present invention there is provided the use of a convertase inhibitor in the manufacture of a medicament for reducing scarring during the healing of wounds or reducing fibrosis in the treatment of fibrotic conditions wherein the medicament is topically applied to the site of a wound or fibrotic disorder.

According to a second aspect of the present invention, there is provided a composition comprising a therapeutically effective amount of a convertase inhibitor and a pharmaceutically acceptable vehicle for the treatment of wounds or fibrosis.

According to a third aspect of the present invention, there is provided a method of treating a subject to reduce or prevent scarring during the healing of wounds; or reduce or prevent fibrosis in the treatment of fibrotic conditions comprising topically administering to a subject in need of such treatment a therapeutically effective amount of a convertase inhibitor.

Convertases are a family of $Ca^{2+}$-dependant serine proteases, otherwise known as SPCs (subtilisin-like pro-protein convertases; see Dubois et al., 1995, Journ. Biol. Chem., 270(18):10618-10624; Sha, X., et al., 1989, Mol. Endocrinology, 3:1090-1098; Chan, S. J., et al., 1992, Proc. Natl. Acad. Sci. USA 89: 6678-6682; and references therein). The inventors have found that the convertase enzyme furin is particularly involved in the activation of mature latent TGF-β at the site of a wound or fibrotic disorder. Although the inventors do not wish to be bound by any hypothesis they believe that convertase activity is able to indirectly stimulate TGF-β activation by modifying the activity of other enzyme(s) with TGF-β activating properties. The inventors believe that the convertase activity contributing to TGF-β activation initially occurs intracellularly, within the platelet, and then continues extracellularly as the platelet contents are released on degranulation. Accordingly convertase inhibitors used according to the present invention are believed to modify activity of this enzyme such that TGF-β activation is reduced.

For the purposes of the specification references to intracellular activity should also be taken to encompass activity within the membranes of cell fragments, such as platelets, except where the context requires otherwise.

The inventors believe that the convertases involved in TGF-β activation are furin-like proprotein convertases. Furins comprise a family of seven transmembrane proprotein convertases produced as an inactive precursor. They must be activated intracellularly, and are involved in pre-protein processing in the trans-Golgi network, at the cell surface, extracellularly and in endosomes. Furins have their effect at arginine-containing cleavage sites, the minimal site being Arg-X-X-Arg. Relevant reviews include Molloy et al, 1999; Shapiro et al. 1997 (J. Histochem. Cytochem. 45:3-12) and Pearton et al. 2001 (Experimental Dermatology 10:193-203).

Platelets are a major source of TGF-β in the circulation and release latent TGF-β when the platelet is activated (e.g. in response to injury). During the healing process, various forms of TGF-β are to be found at a wound site or site of a fibrotic disorder. These different forms are active TGF-β (which is in its free form), the small latent complex (TGF-β-latency associated peptide), and the large latent complex (TGF-β-latency associated peptide-latent TGF-β binding protein). The different complexes undergo different fates and perform different roles during the healing process. In particular, the large and small latent complexes are activated by cleaving in order to release active TGF-β whilst the healing process occurs.

The prior art suggests that cleavage of the large and small latent complexes at a wound site is mediated by plasmin. Furthermore, convertases such as furin are believed to be responsible for the intracellular processing of pro-TGF-β within megakaryocytes (which give rise to platelets) in the bone marrow. This processing of pro-TGF-β involves cleavage and folding of the pro-protein to produce the mature form. The mature form produced is not, however, "active" TGF-β, and may be associated with the large or small latent complexes. Accordingly convertases have not previously been thought to play a part in the activation of latent TGF-β (such as TGF-β in the small latent complex) from platelets in the blood at a site of a wound or fibrotic disorder.

However, the inventors have established (as described in more detail in the Example) that, surprisingly, activity of convertase enzymes such as furin effects the extracellular activation of TGF-β at a wound site. Hence by inhibiting the activity of convertase enzymes at a wound site or site of a fibrotic disorder it is possible to reduce the amount of active TGF-β at such a site and thereby reduce scarring and/or fibrosis. It is interesting to note that this activity of convertases appears to occur intracellularly and extracellularly. Furthermore the activity does not appear to be associated with, or controlled by, transcriptional regulation (in contrast to known convertase activity in cells such as megakaryocytes) and thus is able to take place in the anuclear platelet, or even extracellularly.

The novel observation that convertase enzymes are involved in activation of TGF-β is in contrast to the previously reported role of these enzymes in TGF-β processing and maturation, and opens a range of therapeutic possibilities that could not have been envisaged before.

Although the prior art recognises that platelets contain latent TGF-β it provides no indication that it is possible to prevent activation of this TGF-β by inhibiting convertase activity.

Instead the prior art only suggests that inhibitors of convertase are able to inhibit the processing and maturation that produces latent TGF-β. This activity of convertases is transcriptionally regulated. Thus the skilled person would have recognised that once latent TGF-β is present in circulating platelets convertase inhibitors would not be able to influence its state.

It is only with the present invention that it can be seen that convertase inhibitors are able to prevent the activation, and undesirable effects, of this platelet-borne latent TGF-β at a wound site.

The efficacy of convertase inhibitors for reducing scarring or fibrosis is enhanced by the fact that the latent TGF-β released by platelets is almost entirely composed of TGF-$β_1$ (associated with the small latent complex). It is well known that TGF-$β_1$ is a key factor in wound healing and is pro-fibrotic favouring scar formation. The preponderance of the pro-fibrotic TGF-β isoforms during the early phases of wound healing (which causes local conditions that favour scar formation and fibrosis) is in large measure due to platelet-mediated growth factor release. With time the ratio of TGF-β isoforms changes as levels of platelet-derived TGF-$β_1$ decrease and there is an increase in the levels of anti-fibrotic TGF-$β_3$ derived from fibroblasts. Preventing the activation of latent TGF-$β_1$ according to the present invention can therefore dramatically reduce the degree of scarring associated with wound healing.

Several classes of compound may be used according to the invention as convertase inhibitors. These compounds include:
(i) compounds that bind to convertase enzymes and inhibit its activity (e.g. competitive inhibitors or allosteric inhibitors);
(ii) compounds which prevent the transcription, translation or expression of convertase enzymes (e.g. ribozymes or antisense DNA molecules);
(iii) compounds which increase the rate of degradation of convertase enzymes;
(iv) compounds which inhibit the interaction of convertase enzymes with latent TGF-β and/or with TGF-β activating proteins;
(v) compounds which inhibit the proteolytic activation of the inactive furin precursor; and
(vi) compounds which inhibit a potential intracellular translocation of convertase enzymes, such as furin or PACE-4, to subcellular sites of activity.

In one embodiment of the invention it is preferred that the convertase inhibitor is an inhibitor of furin.

In a further embodiment of the invention it is preferred that the convertase inhibitor is an inhibitor of furin-like proprotein convertases, and more preferably an inhibitor of PACE-4.

The convertase inhibitor may be a serine protease inhibitor and is preferably a thiol inhibitor. The thiol inhibitor may be a peptidyl chloroalkylketone having a peptide moiety which mimics at least one convertase enzyme cleavage site. It has been found that peptidyl chloroalkylketones with peptide moieties that mimic the convertase enzyme cleavage site are specific inhibitors of the enzymatic activity. A preferred inhibitor is decanoyl-RVKR-cmk (SEQ ID NO:1) and derivatives thereof.

Further convertase inhibitors suitable for use according to the invention include:
(i) alpha 1-antitrypsin (α-1 PDX), or nucleic acids encoding the same;
(ii) derivatives of alpha 1-antitrypsin such as those comprising the amino acid sequences arg-val-pro-arg (SEQ ID NO: 4), ala-val-arg-arg (SEQ ID NO: 5) or arg-val-arg-arg (SEQ ID NO: 6), or nucleic acids encoding the same;
(iii) p-chloromercuribenzoate;
(iv) tosylamido-phenylethyl chloromethyl ketone (TPCK);
(v) D-polyarginines (e.g. hexa-arginine (SEQ ID NO: 7) and its derivatives);
(vi) Acetyl-leu-leu-arg-aldehyde hemisulfate;
(vii) S-carboxyphenylethyl-carbamoyl-arg-val-arg-aldehyde;
(viii) Threodimercaptobutanediol; and
(ix) Tos-Lys-chloromethylketone.

Alternatively and/or in addition, the convertase inhibitor may sequester $Ca^{2+}$. Furthermore a Ca2+ sequester (such as EDTA or EGTA) may be used in conjunction with inhibitors such as those mentioned above.

The inventors have established that convertase enzymes act, both extracellularly and intracellularly, to cause the activation of latent TGF-β in the extracellular space at the site of a wound or a fibrotic condition. This led them to realise that it is possible to use convertase inhibitors applied topically to prevent the activation of latent TGF-β associated with wound healing or fibrosis. The prior art suggests that the activity of convertases such as furin takes place in the megakaryocytes in the bone marrow that give rise to platelets, and that this activity is limited to the processing that produces latent TGF-β. Accordingly the prior art contains no teaching that suggests that local inhibition of furin activity would inhibit the conversion of latent TGF-β to active TGF-β. Furthermore the prior art suggest that therapeutic manipulation of furin would require an agent that may be delivered to, and achieve its action in, the bone marrow.

The surprising finding that extracellular convertase activity contributes to TGF-β activation led the inventors to realise that water-soluble convertase inhibitors may be used to decrease TGF-β activation, and thus reduce scarring. The use of water-soluble inhibitors, which cannot penetrate the cell membrane, is particularly advantageous since such inhibitors generally exhibit low levels of cytotoxicity. Water-soluble convertase inhibitors can also be readily formulated into compositions that induce minimal inflammatory reactions, an important consideration when designing anti-scarring agents. A preferred water-soluble convertase inhibitor suitable for use according to the invention is L-hexaarginine (SEQ ID NO: 7).

The effects of localised inhibition of convertase activity are very different from those that would arise as a result of systemic administration of convertase inhibitors. Even were a skilled person to suggest that systemic use of convertase inhibitors would indirectly reduce levels of active TGF-β by inhibiting processing of pro-TGF-β in the bone marrow they would also understand that such an approach would have a number of deleterious effects. One such effect would be that systemic administration of convertase inhibitors would also reduce the level of anti-fibrotic TGF-$β_3$ that is important in the later stages of wound healing. A second problem is that systemic use of convertase inhibitors would have detrimental, and possibly toxic, effects since convertases are involved in the normal processing of proteins other than TGF-β.

Neither of these disadvantages is applicable to the topical application of convertase inhibitors according to the invention. In this use the effect of the inhibitors is directed to the region of the wound, or site of fibrosis, and the administration of the inhibitors may be timed so that only the initial quantities of TGF-β released from platelets are affected.

As set out above, the inventors believe that the convertase activity contributing to TGF-β activation is initiated within the platelets, and that the extracellular convertase activity occurs as a result of convertases being released into the extracellular space on de-granulation of the platelets. As a result, inhibitors of convertase activity for use according to the invention may be inhibitors that are able to cross the cell membrane and act intracellularly. Such inhibitors are able to reduce convertase activity prior to de-granulation. They may be able to decrease TGF-β activation occurring both intracellularly and extracellularly. That said, it appears that the majority of convertase activity contributing to TGF-β activation occurs extracellularly after platelet degranulation. Thus water-soluble inhibitors may be used to effectively reduce TGF-β activation and thus reduce scarring and/or fibrosis.

In a preferred embodiment of the invention the medicament containing the convertase inhibitor may be applied prophylactically. Thus the medicament may be applied to a site where a wound may be formed or fibrosis may occur (e.g. before elective surgery).

The inventors find that the inhibitors according to the present invention are highly suited for topical application to dermal wounds or dermal fibrotic conditions.

Convertase inhibitors used according to the invention may be proteins or have peptidyl components. Such proteins can easily be modified (for instance by amino acid addition, substitution or deletion) to form derivatives that retain the ability to inhibit enzymes such as film. Therefore derivatives that retain functional characteristics of naturally occurring proteins are also preferred inhibitors of the invention. Examples of such derivatives include functionally active fragments of naturally occurring proteins and even precursors of naturally occurring proteins (e.g. proproteins) which are activated in situ.

Convertase inhibitors may be used according to the invention in situations or conditions where scarring needs to be prevented or reduced such as:

(i) where scars of the skin may be excessive and/or detrimental to tissue function and particularly when scar contracture occurs or may occur (for instance skin burns and wounds which impair flexibility of a joint and particularly scarring in children);

(ii) scarring to the skin when cosmetic considerations are important;

(iii) when hypertrophic or keloid scars particularly in Afro-Caribbean and Mongoloid races) may occur which can cause functional and cosmetic impairment;

(iv) scarring resulting from skin grafts in both donor sites and from the application of artificial skin;

(v) scarring within the central nervous system (e.g. following neuro-surgery or penetrating injuries of the brain), for example glial scarring can prevent reconnection of severed neurons;

(vi) scarring in the eye and particularly of the cornea (scarring can result in abnormal opacity and lead to problems with vision or even blindness), in the retina (scarring can cause buckling or retinal detachment and consequently blindness) and scarring following wound healing in operations to relieve pressure in glaucoma (e.g. glaucoma filtration surgery) which can result in the failure of the surgery whereby the aqueous humour fails to drain and hence the glaucoma returns;

(vii) scarring in the heart (e.g. following surgery or myocardial infarction) which can give rise to abnormal cardiac function;

(viii) scarring of the gut such as may occur following operations involving the abdomen or pelvis that result in adhesion between viscera (adhesions between elements of the gut and the body wall can form and cause twisting in the bowel loop leading to ischaemia, gangrene and the necessity for emergency treatment-untreated they may even be fatal); likewise, trauma or incisions to the guts can lead to scarring and scar contracture or strictures which cause occlusion of the lumen of the guts which again can be life threatening;

(ix) scarring in the pelvis in the region of the fallopian tubes which can lead to infertility, (x) scarring following injury to muscles which can result in abnormal contraction and hence poor muscular function;

(xi) scarring or fibrosis following injury to tendons and ligaments which can result in serious loss of function.

The convertase inhibitors may also be used for the treatment or prevention of fibrosis. For instance the compounds may be used to treat fibrotic disorders such as cirrhosis of the liver, liver fibrosis, glomerulonephritis, pulmonary fibrosis, scleroderma, myocardial hibernation, fibrosis following myocardial infarction, central nervous system fibrosis following a stroke or neuro-degenerative disorders (e.g. Alzheimer's Disease), proliferative vitreoretinopathy (PVR), restenosis and arthritis.

The convertase inhibitors are useful for reducing or preventing fibrosis in fibrotic diseases and for reducing or preventing the formation of fibrosis that manifests as hypertrophic scarring (particularly of the skin) or keloids.

Wound healing compositions used according to the invention may take a number of different forms depending, in particular on the manner in which they are to be used. Thus, for example, they may be in the form of a liquid, ointment, cream, gel, hydrogel, powder or aerosol. All of such compositions are suitable for topical application to skin, which is a preferred means of administering convertase inhibitors to a subject (person or animal) in need of treatment.

The convertase inhibitors may be provided on a sterile dressing or patch which may be used to cover or even pack a wound to be treated.

A preferred composition of the invention may be in the form of an injectable solution (e.g. for intradermal injection around the margins of a wound or a site to be wounded).

It will be appreciated that the vehicle of the composition of the invention should be one which is well tolerated by the patient and allows release of the active convertase inhibitor to the wound. Such a vehicle is preferably biodegradeable, bioresolveable and/or non-inflammatory.

The composition of the invention may be used in a number of ways. Thus, for example, a composition may be applied in, and/or around a wound of a patient to regulate wound healing. If the composition is to be applied to an "existing" wound, then the pharmaceutically acceptable vehicle will be one which is relatively "mild" i.e. a vehicle which is biocompatible, biodegradable, bioresolvable and non-inflammatory.

It is also possible to use compositions in accordance with the invention prior to surgery (particularly elective surgery) so as to provide for regulation of healing of the subsequently formed surgical wound. In this case the vehicle of the topically applied composition may need to be one capable of going across the keratinous layer of the skin. Examples of suitable vehicles for this purpose include dimethyl sulphoxide and acetic acid. Such prophylactic use is a preferred use of convertase inhibitors according to the invention.

The compositions are suitable to be used for reducing or controlling scarring resulting form surgical operations on the eye (e.g. laser surgery on the cornea). In this case the composition or medicament may be in the form of an eye drop.

Convertase inhibitors may be used in a range of internal wound healing applications. Thus for example, the composition may be formulated for inhalation for use in wound healing of the lungs or for the prevention or treatment of fibrosis and strictures in the lung.

It will be appreciated that the amount of a convertase inhibitor to be applied to the wound site depends on a number of factors such as the biological activity and bioavailability of the compound, which in turn depends on the mode of administration and the physicochemical properties of the inhibitor. Other factors may include:

A) The half-life of the inhibitor in the subject being treated.
B) The specific condition to be treated.
C) The age of the subject.

The frequency of administration will also be influenced by the above mentioned factors and particularly the half-life of the convertase inhibitor within the subject being treated.

Generally when the compositions are used to treat existing wounds or fibrotic disorders the convertase inhibitor should be administered as soon as the wound has occurred or the disorder has been diagnosed. Therapy with the composition should continue until the wound has healed to a clinician's satisfaction or, in the case of a fibrotic disorder, the risk or cause of abnormal fibrous tissue formation has been removed.

Compositions which modulate scarring and/or fibrotic disorders should also be applied to a wound as soon as possible after the wound has formed. However scars and fibrosis can develop over days or even weeks. Therefore the subject being treated may well benefit by administration of a convertase inhibitor even if it is administered days or even weeks after the wound occurred or the disorder developed (or was diagnosed).

When used as a prophylactic (e.g. before surgery or when there is a risk of developing a fibrotic disorder) the convertase inhibitors should be administered as soon as the risk of undesirable fibrosis has been recognised. For instance, a cream or ointment containing a convertase inhibitor may be applied to a site on the skin of a subject where elective surgery is to be performed and decreased scar formation is subsequently desired. In this case, the composition may be applied during the preoperative preparation of the subject or it may even be desirable to apply the composition in the hours or days preceding the surgery (depending upon the health status and age of subject as well as the size of the wound to be formed).

Frequency of administration will depend upon the biological half-life of the inhibitor used. Typically a cream or ointment containing a convertase inhibitor should be administered to a target tissue such that the concentration of the inhibitor at the wound site or tissue affected by a fibrotic condition is maintained at a level suitable for having a therapeutic effect. This may require administration daily or even several times daily.

Known procedures, such as those conventionally employed by the pharmaceutical industry (e.g. in vivo experimentation, clinical trials etc), may be used to establish specific formulations of compositions and precise therapeutic regimes (such as daily doses of the convertase inhibitor and the frequency of administration).

Generally, compositions for use in accordance with the invention should be formulated such that when administered to a wound site or site of a fibrotic disorder that a convertase inhibitor concentration of between 0.01 μM and 10 mM is achieved at the site.

Purely by way of example an injectable solution containing between 0.1 .mu.M and 10 mM of decanoyl-RVKR-cmk (SEQ ID NO:1) is suitable for application to an existing (i.e. "open") wound.

A suitable daily dose of a compound which inhibits convertase activity depends upon the factors discussed above as well as upon the size of the wound, or amount of tissue effected by fibrosis, which is to be treated. Typically the amount of a convertase inhibitor required for the treatment of wounds or fibrotic disorders will be within the range of 0.01 μg to 100 mg of the active compound/24 hours depending upon the size of the wound or extent of fibrosis amongst several other factors.

It will also be appreciated that convertase inhibitors may be isolated from nature or chemically synthesised.

Many known methods of administering convertase inhibitors to a relevant tissue have the disadvantage that it can be difficult to achieve sustained levels of the active convertase inhibitor at a wound site or site of fibrosis over the course of even a few days because convertase inhibitors may have short half-lives in vivo. The half-lives of the convertase inhibitors may be short for a number of reasons which include:

(i) Degradation by proteases and the like.
(ii) Clearance by binding proteins (e.g. α2 macroglobulin).
(iii) Binding and inhibition of agent activity by extracellular matrix molecules such as decorin and fibronectin.

Furthermore, compounds for wound healing and/or treatment of scarring/fibrosis need to be administered in a suitable vehicle and are often provided as a composition comprising the compound and the vehicle. As outlined above, such vehicles are preferably non-inflammatory, biocompatible, bioresorbable and must not degrade or inactivate the active compound (in storage or in use). However, it can often be difficult to provide a satisfactory vehicle for delivering specific compounds to a tissue to be treated.

A convenient way in which these problems can be obviated or mitigated is to provide at a wound site (or site of fibrosis) a therapeutically effective amount of protein or peptide convertase inhibitor by gene therapy.

According to a fourth aspect of the present invention there is provided a delivery system for use in a gene therapy technique, said delivery system comprising a DNA molecule encoding for a protein which inhibits convertase activity, said DNA molecule being capable of being transcribed to lead to the expression of said protein.

According to a fifth aspect of the present invention there is provided the use of a delivery system as defined in the preceding paragraph for use in the manufacture of a medicament for use in the treatment of wounds or fibrosis.

According to a sixth aspect of the present invention there is provided a method of treating a wounds or fibrosis comprising administering to a patient in need of treatment a therapeutically effective amount of a delivery system as defined for the fifth aspect of the invention.

The delivery systems according to the invention are highly suitable for achieving sustained levels of a convertase inhibitor at a wound site or site of fibrosis over a longer period of time than is possible for most conventional delivery systems. Protein may be continuously expressed from cells at the wound site or site of fibrosis that have been transformed with the DNA molecule of the invention. Therefore, even if the protein has a very short half-life as an agent in vivo, therapeutically effective amounts of the protein may be continuously expressed from the treated tissue.

Furthermore, the delivery system of the invention may be used to provide the DNA molecule (and thereby the protein which is an active therapeutic agent) without the need to use conventional pharmaceutical vehicles such as those required in ointments or creams that are contacted with the wound.

The delivery system of the present invention is such that the DNA molecule is capable of being expressed (when the delivery system is administered to a patient) to produce a protein which directly or indirectly has activity for wound healing and/or treatment of fibrosis or scarring by inhibiting convertase activity. By "directly" we mean that the product of gene expression per se has the required activity for wound healing and/or regulating fibrosis or scarring. By "indirectly" we mean that the product of gene expression undergoes or mediates (e.g. as an enzyme) at least one further reaction to provide an agent effective for wound healing and/or regulating fibrosis or scarring by inhibiting convertase activity.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors may be designed such that the vector will autonomously replicate in the nucleus of the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one which becomes incorporated in the DNA of cells of the subject being treated. Undifferentiated cells may be stably transformed leading to the production of genetically modified daughter cells. When this is the case, regulation of expression in the subject may be required e.g. with specific transcription factors, gene activators or more preferably with inducible promoters which transcribe the gene in response to a signal specifically found at a wound site. Alternatively, the delivery system may be designed to favour unstable or transient transformation of differentiated cells in the subject being treated. In this instance, regulation of expression may be less important because expression of the DNA molecule will stop when the transformed cells die or stop expressing the protein (ideally when the wound, fibrosis or scarring has been treated or prevented).

The delivery system may provide the DNA molecule to the subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to the wounded area topically or by injection.

The protein expressed from the DNA molecule may be one which directly or indirectly provides for wound healing with reduced scarring or one which serves to regulate (inhibit, prevent or reverse) fibrosis.

It will be appreciated that the delivery system according to the fifth aspect of the invention may be used according to the sixth or seventh aspects of the invention to treat any of the conditions hereinbefore described.

The present invention will further be described in the following non-limiting Example which refers to the accompanying drawing, in which.

EXAMPLE

The ability of inhibitors of furin activity to inhibit activated platelets' production of active TGF-β was demonstrated by the ability of the inhibitors to abrogate the platelet's release and activation of TGF-β in response to stimulation with thrombin. The experimental protocol was as set out below.

1. Protocols.

Collection and Preparation of Human Platelets:

Peripheral venous blood samples from healthy adult volunteers (aged 21 to 45) were taken into 20-gauge S-Monovettes. EDTA was used to prevent coagulation of the samples. Human platelets were isolated by differential centrifugation according to the following protocol:

Blood samples were centrifuged at 300 g for 10 minutes to produce a supernatant of platelet rich plasma. Platelet rich plasma was then centrifuged at 2,500 g for 15 minutes to produce a pellet of platelets. Platelets were harvested from the pellet and resuspended prior to use.

Production of Platelet Hypotonic Lysates:

Platelets collected as described above were resuspended in distilled water and incubated at room temperature for 5 minutes. Lysis was stopped by addition of an equal volume of 2× serum-free DME medium containing 0.2% pyrogen poor bovine serum albumen. The lysate was cleared by centrifugation at 12,000 g for 10 minutes at room temperature before use.

2. Experimental Results 1.

2.1. Platelets Activated with Thrombin Release and Activate TGF-β:

Human platelets collected as outlined above were activated by the addition of thrombin (0.1 u/ml for 30 minutes at 37° C.). This activation caused the release of large amounts of TGF-β from the platelets (total TGF-β 60.2 ng/ml average), and also triggered the generation of significant amounts of active TGF-β (159 pg/ml on average if the platelets were static during activation, 896 pg/ml on average if the platelets were subjected to agitation during activation) in the platelet releasates as assayed using the PAI/L bioassay for TGF-β described by Abe et al. ("An assay for transforming growth factor-β using cells transfected with a plasminogen activator inhibitor-1 promoter-luciferase construct" 1994, Anal. Biochem. 216: 276-284). Pan-specific neutralising anti-TGF-β antibodies completely abolished the signal obtained in the PAI/L assay verifying that active TGF-β was measured. Activation of latent TGF-β was platelet-mediated, since exogenous thrombin added to platelet releasates was unable to activate latent TGF-β directly (data not shown). Antibody inhibition experiments confirmed that platelets expressed exclusively TGF-$β_1$ (data not shown).

2.2. Platelets Contain Intracellular Active TGF-β:

The presence of active TGF-β within platelets was confirmed by both immuno-localisation and bioassay studies.

Confocal microscope immuno-fluorescence studies of the localisation of active TGF-β within platelets were carried out using the chicken derived active TGF-β1-specific IgY AF-101-NA (R&D Systems) and an antibody specifically reactive with the membrane marker CD41 (BD Biosciences). Subcellular localisation of these proteins was investigated in optical sections collected at 0.5 μm intervals along the z-axis. TGF-β1 was demonstrated to be present, and to have an intracellular localisation (lying within that of the membrane marker CD41).

The PAI/L bioassay for TGF-β was used to validate the presence of active TGF-β in platelets through assaying for the presence of active TGF-β in hypotonic lysates of human platelets (prepared as described above).

In lysates derived from resting platelets 99% of the total TGF-β present (total TGF-β 34.7 ng/ml) was the latent form, although a significant proportion of active TGF-β (104 pg/ml) was detected. In lysates derived from thrombin activated platelets the mean total TGF-β was 19.5 μg/ml, of which 151 pg/ml was active.

The results of the bioassay thereby confirmed the immuno-localisation finding that platelets contain active TGF-β.

2.3. Inhibition of Furin Activity Inhibits TGF-β Activation by Thrombin Activated Platelets:

In a comparative experiment the ability of inhibitors of known activators of TGF-β (such as TSP-1, plasmin, M6P/IGF-II receptor) and putative activators of latent TGF-β such as other serine proteinases, cysteine proteinases, calpain I and II, caspase-3, and furin) to block latent TGF-β activation in human platelets was assessed.

Figure 1:
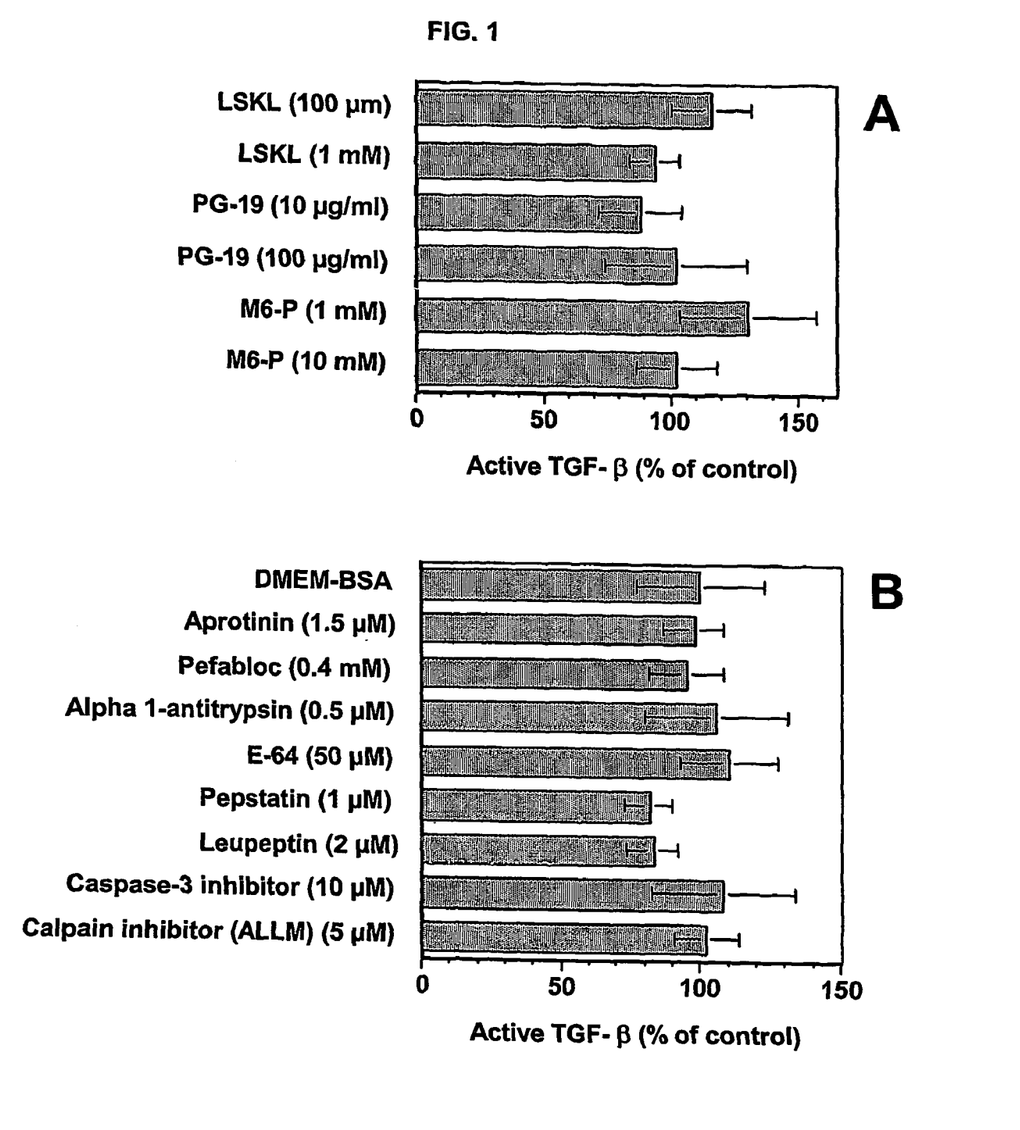
FIG. 1 illustrates the results of analysis of the ability of different inhibitors, and putative inhibitors, of TGF-β activation to prevent TGF-β activation by platelets. 'LSKL' is disclosed as SEQ ID NO: 8 and 'dec-RVKR-cmk' is disclosed as SEQ ID NO: 1.

Human platelets were pre-incubated with the inhibitors (listed below) prior to stimulation with thrombin (as above), and active and total TGF-β levels were determined in the platelet releasates using the PAI/L assay (as above). The results are shown in FIG. 1, panels A to C.

The results showed that latent TGF-β activation was not significantly affected by the presence of inhibitors specific for TSP-1 (LSKL peptide (SEQ ID NO: 8)), plasmin (neutralising monoclonal antibody, PG19—a neutralising antibody provided by Dr. Michael Kramer), or M6P/IGF-II receptor (M6P-mannose-6-phosphate) (panel A). Moreover, a number of inhibitors (aprotinin, pefabloc, α1-antitrypsin, E-64, pepstatin, leupeptin, caspase-3 inhibitor and calpain inhibitor) of other proteinases potentially involved in platelet-mediated latent TGF-β activation also proved to be ineffective (panel B).

In comparison platelet incubation with a membrane-permeable inhibitor of furin-like proprotein convertases, dec-RVKR-cmk (SEQ ID NO:1) (decanoyl-Arg-Val-Lys-Arg-chloromethyl ketone-Bachem), drastically reduced the generation of active TGF-.beta. in releasates as well as intracellularly in a dose-dependent fashion (panel C). (intracellular measurements were taken from hypotonic lysates). The inventors believe that the residual TGF-.beta. present (approximately 20-30%) was activated prematurely during platelet preparation prior to the addition of the inhibitor.

2.4. Summary.

The above results indicate that platelet-mediated latent TGF-β activation surprisingly occurs extracellularly at the site of platelet activation (i.e. a wound site or a site of a fibrotic condition) and involves proteolytic processing by a furin-like convertase enzyme. They further show that the activation of latent TGF-β by platelets can be successfully inhibited by treatment of the platelets with an inhibitor of furin activity which may be applied topically.

As skilled person will appreciate from these results that convertase inhibitors may be used to inhibit TGF-$β_1$ activation and will thereby be effective as anti-scarring or anti-fibrotic agents.

3. Experimental Results 2.

3.1. Furin-Like Enzymes are Involved in Platelet-Mediated Latent TGF-Activation.

Platelets were activated with thrombin in the absence or presence of furin inhibitors. Platelets were pre-incubated with hexaarginine (SEQ ID NO: 7), whereas dec-RVKR-cmk (SEQ ID NO:1) was added 5 mm after thrombin addition because of interference with platelet activation at higher concentrations. Active and total TGF-β in releasates were determined in the PAI/L bioassay. The results are shown in panel A of FIG. 2. Active TGF-β levels in the controls were 82 pg/ml (dec-RVKR-cmk (SEQ ID NO:1) data) and 61 pg/ml (hexaarginine (SEQ ID NO: 7) data), total TGF-β levels were 33.4 ng/ml (dec-RVKR-cmk (SEQ ID NO:1) data) and 39.5 ng/ml (hexaarginine (SEQ ID NO: 7) data).

In a further experiment, furin inhibitors were added to platelet-free releasates of activated platelets, and activation was allowed to continue in the absence of platelets for 30 mm at 37° C. The results of this experiment are shown in panel B of FIG. 2. Active TGF-β levels in the controls were 77 pg/ml (dec-RVKR-cmk data (SEQ ID NO:1)) and 104 pg/ml (hexaarginine data (SEQ ID NO: 7)). Incubation on ice reduced activation in the controls to approximately 56% (data not shown). Data represent the mean values of three independent experiments assayed in triplicate.

Figure 2:
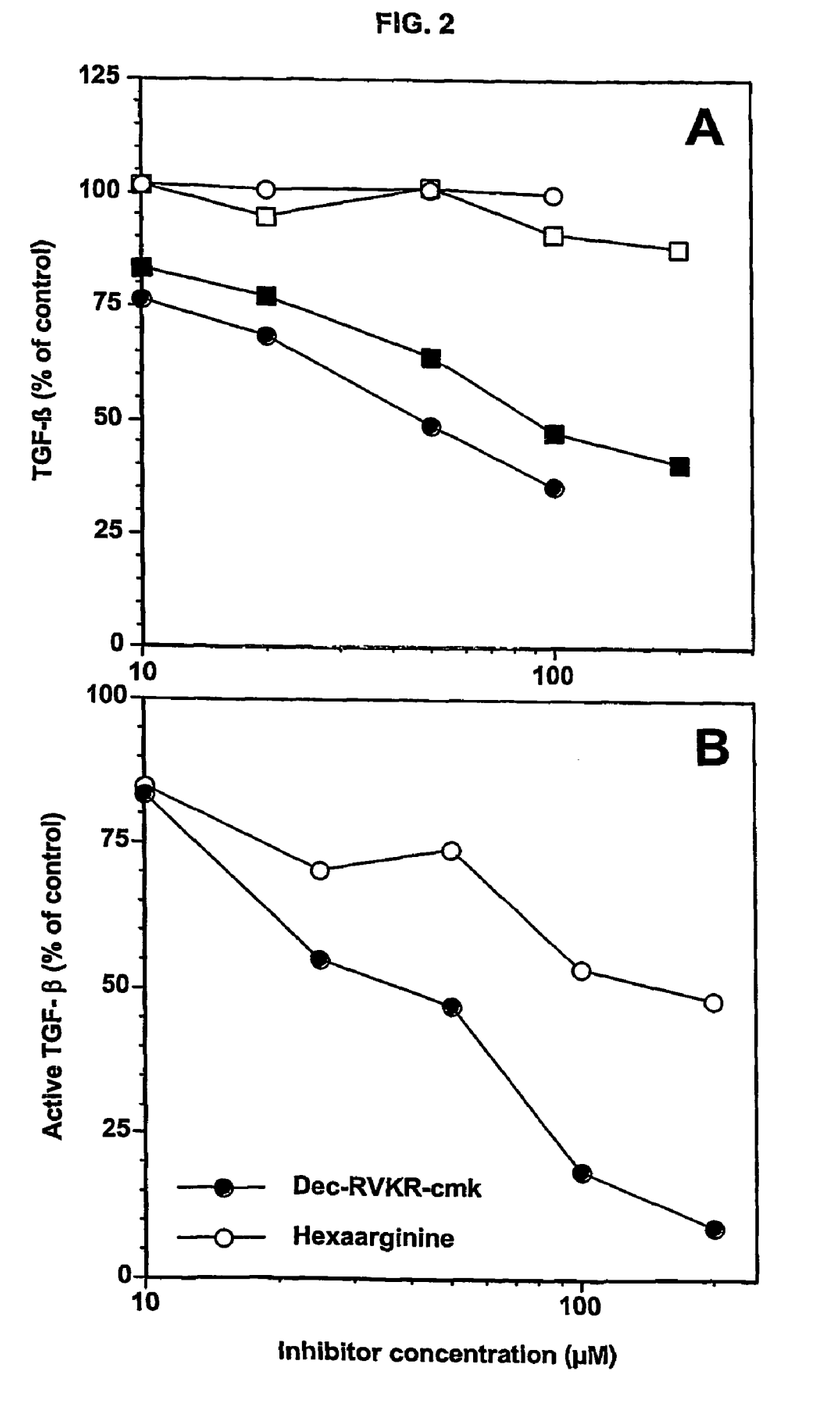
FIG. 2 illustrates the effect of Dec-RVKR-cmk (SEQ ID NO:1) and hexaarginine (SEQ ID NO: 7) in: A platelet releasates; and B platelet-free releasates as referred to in experimental results section 2 of the example. In A ■ indicates active hexaarginine (SEQ ID NO: 7) and □ indicates total hexaarginine (SEQ ID NO: 7) whereas indicates active dec-RVKR-cmk (SEQ ID NO:1) and ○ indicates total dec-KR RVKR-cmk (SEQ ID NO:2). In panel B ○ indicates hexaarginine (SEQ ID NO: 7) whereas ● indicates dec-RVKR-cmk (SEQ ID NO:1)

The results illustrate that incubation of thrombin-stimulated platelets with the membrane-permeable protease inhibitor, dec-RVKR-cmk (SEQ ID NO:1), considerably reduces the generation of active TGF-.beta. in releasates (FIG. 2 panel A). Dec-RVKR-cmk (SEQ ID NO:1) is a specific and potent inhibitor of subtilisin/Kex2p-like proprotein convertases, with its peptide sequence being based on the substrate recognition sequence of these enzymes.

The most prominent and ubiquitously expressed member of this endoprotease family is furin, which typically cleaves at the consensus sequence motif R-X-(K/R)-R. The membrane-impermeable furin inhibitor, hexa-L-arginine (SEQ ID NO: 7), also significantly reduced active TGF-β in releasates (FIG. 2 panel A) indicating that at least part of the activation occurred extracellularly following latent TGF-β release.

Latent TGF-β activation appeared to be enzymatic and independent of the continuous presence of platelets, since incubation of platelet-free releasates on ice (as compared to 37° C.) reduced active TGF-β levels to approximately 56%. As observed for platelet suspensions, activation in releasates was inhibited, in a dose-dependent fashion, by the furin inhibitors, dec-RVKR-cmk (SEQ ID NO:1) and hexa-L-arginine (SEQ ID NO: 7) (FIG. 2B). This indicates that the furin-like enzyme involved in latent TGF-β activation is released from activated platelets.

3.2. Platelets Contain and release Furin-Like Enzyme Activity.

Releasates or hypotonic lysates of activated platelets were assayed using the furin substrate, pyr-RTKR-amc (SEQ ID NO:3) in the absence or presence of the furin inhibitors, hexaarginine (SEQ ID NO: 7) (200 μM) or dec-RVKR-cmk (SEQ ID NO:1) (150 μM). Values were corrected for substrate-independent endogenous fluorescence (control without substrate) as well as for spontaneous substrate hydrolysis (buffer control). Mean values±S.E.M. of 2-3 separate experiments assayed in duplicate are shown.

Figure 3:
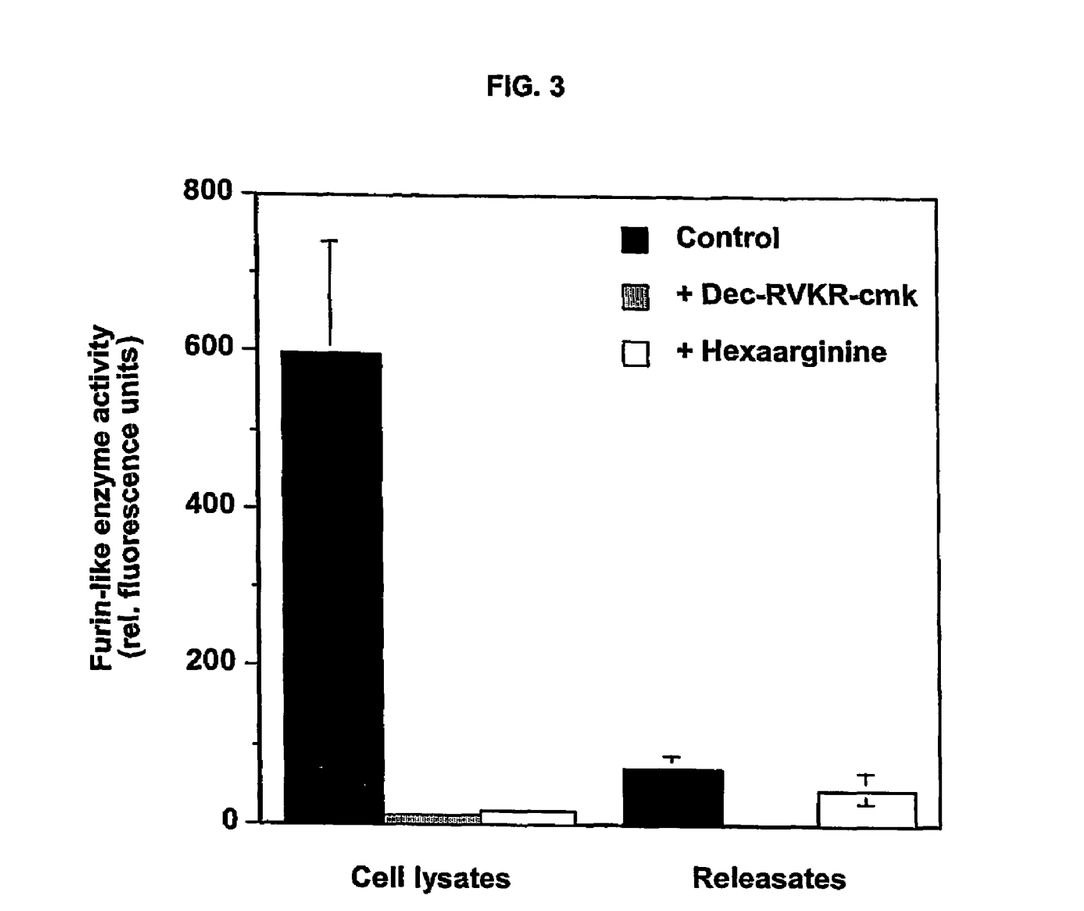
FIG. 3 illustrates the effect of furin inhibitors on furin activity in cell lysates and releasates for control samples (■); dec-RVKR-cmk (SEQ ID NO:1) (▣); and hexaarginine (SEQ ID NO: 7) (□) in experimental results section 2 of the example.

The presence of furin-like enzyme activity in both hypotonic lysates and releasates of human platelets was analysed using the fluorogenic furin substrate, pyr-RTKR-amc (SEQ ID NO:3). Platelet lysates contained a furin-like enzyme activity, part of which (approximately 12%) was released upon thrombin stimulation. Enzyme activity in cell lysates and releasates was inhibited by dec-RVKR-cmk (SEQ ID NO:1) and hexa-L-arginine (SEQ ID NO: 7) (FIG. 3).

The extracellular generation of active TGF-β by thrombin-stimulated human platelets was significantly reduced in the presence of inhibitors of furin-like proprotein convertases.

3.3 Summary.

Furin-like proprotein convertases catalyze the maturation of pro-TGF-β precursor to heat-activatable latent growth factor complex. Our data indicate, however, that platelet β-granules contain and release mature, heat-activatable latent TGF-β, and that the levels are not affected by furin inhibitors. Thus, pro-TGF-β processing in the megakaryocytic lineage occurs in the megakaryocytes. These data therefore identify a novel function of furin-like enzymes, namely involvement in the extracellular activation of platelet large latent TGF-$β_1$ complex under physiological conditions.

In summary, the inventors found that platelets are not only major storage sites for latent TGF-β1 but also activate part of it following degranulation. While the mechanism of activation does not require any of the well-characterized activators, TSP-1, M6P/IGF-II receptor, or plasmin, the platelet latent TGF-β complex appears to be activated via a sequence of events by a furin-like convertase released by the platelets. Following release in vivo, this enzyme appears to continue to operate, independently of the presence of platelets, in the surrounding tissue (e.g. the wound area), leading to the activation of extracellular-matrix associated latent TGF-β complex. Therefore, this novel mechanism of activation represents a target to modulate TGF-β activity in pathologic conditions involving platelet degranulation, such as wound repair, fibrosis, arteriosclerosis, and cancer. Therefore the inventors have found that inhibitors according to the invention (such as decanoyl-RVKR-cmk (SEQ ID NO:1) and hexa-arginine (SEQ ID NO: 7) may be used according to the invention).

The invention claimed is:

1. A method for reducing scar formation during the healing of at least one wound in a subject who has incurred injuries that result in said at least one wound or in a subject who will be inflicted with at least one surgical wound at a known site comprising applying a furin inhibitor, wherein the furin inhibitor is decanoyl-RVKR-cmk, directly to the site of said wound.

2. The method of claim 1 wherein said injury is to a muscle, tendon, ligament or skin.

3. The method of claim 1 wherein the wound is a surgical wound.

4. The method of claim 1 wherein said applying is topical.

5. The method of claim 1 wherein said applying is by injection.

* * * * *

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Val Lys Arg
1

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Arg Arg Val Lys Arg
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Arg Thr Lys Arg
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Val Pro Arg
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Val Arg Arg
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Val Arg Arg
1

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Arg Arg
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ser Lys Leu
1
```